(12) United States Patent
Mouri

(10) Patent No.: US 9,238,130 B2
(45) Date of Patent: Jan. 19, 2016

(54) MEDICAL CONNECTOR

(71) Applicant: Terumo Kabushiki Kaisha, Tokyo (JP)

(72) Inventor: Takayuki Mouri, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 1 day.

(21) Appl. No.: 13/964,555

(22) Filed: Aug. 12, 2013

(65) Prior Publication Data

US 2013/0331692 A1 Dec. 12, 2013

Related U.S. Application Data

(63) Continuation of application No. PCT/JP2011/079651, filed on Dec. 21, 2011.

(30) Foreign Application Priority Data

Feb. 25, 2011 (JP) ................................. 2011-039159

(51) Int. Cl.
*A61M 25/16* (2006.01)
*A61M 39/10* (2006.01)
(Continued)

(52) U.S. Cl.
CPC ........... *A61M 39/1055* (2013.01); *A61M 39/10* (2013.01); *A61M 25/0097* (2013.01); *A61M 25/0105* (2013.01); *A61M 39/105* (2013.01)

(58) Field of Classification Search
CPC .......... A61M 39/1055; A61M 39/105; A61M 25/0097
USPC ........................... 604/533–534, 241, 538, 284
See application file for complete search history.

(56) References Cited

U.S. PATENT DOCUMENTS 4,886,507 A * 12/1989 Patton et al. .................. 604/284
4,931,049 A *  6/1990 Klimas ..................... 604/165.01
5,125,915 A    6/1992 Berry
(Continued)

FOREIGN PATENT DOCUMENTS

CN       1477762 A    3/2006
CN     101639145 A    2/2010
(Continued)

OTHER PUBLICATIONS

International Search Report from the International Bureau of WIPO for International Application No. PCT/JP2011/079651 dated Apr. 3, 2012 and English translation of the same (3 pages).
(Continued)

*Primary Examiner* — Edelmira Bosques
(74) *Attorney, Agent, or Firm* — Fitch Even Tabin & Flannery LLP

(57) ABSTRACT

A medical connector and method of using the medical connector are provided. In one form, the medical connector includes an elongate main body having a longitudinal axis and a lumen extending axially therethrough, proximal and distal end portions of the elongate main body with the distal end portion being configured to be connected to a first tubular medical device, an auxiliary connection device having a port for being connected to a second tubular medical device, and an adjustable connection between the auxiliary connection device and the elongate main body that allows positioning of the port of the auxiliary connection device relative to the elongate main body to be adjustably selected by a user for ease in connecting the second tubular medical device to the auxiliary connection device.

12 Claims, 7 Drawing Sheets

(51) Int. Cl.
*A61M 25/00* (2006.01)
*A61M 25/01* (2006.01)

(56) References Cited

U.S. PATENT DOCUMENTS

| | | | | |
|---|---|---|---|---|
| 5,129,887 | A | * | 7/1992 | Euteneuer et al. ............ 606/194 |
| 5,156,596 | A | * | 10/1992 | Balbierz et al. .......... 604/164.11 |
| 6,579,261 | B1 | | 6/2003 | Kawamura |
| 2006/0027270 | A1 | * | 2/2006 | Truitt .................... A61M 39/02 137/843 |
| 2006/0284423 | A1 | | 12/2006 | Katsuno |
| 2009/0124983 | A1 | | 5/2009 | Ferrari |
| 2010/0280463 | A1 | | 11/2010 | Murayama et al. |

FOREIGN PATENT DOCUMENTS

| | | |
|---|---|---|
| CN | 101909688 A | 12/2010 |
| JP | H07-114813 A | 12/1995 |
| JP | 2003-062089 A | 3/2003 |
| JP | 4472310 B | 3/2010 |

OTHER PUBLICATIONS

English translation of Chinese Office Action dated Jul. 1, 2014 for 201180057745.6. (8 pages).

Chinese Office Action dated Mar. 12, 2015 for 201180057745.6. and English translation of the same.

* cited by examiner

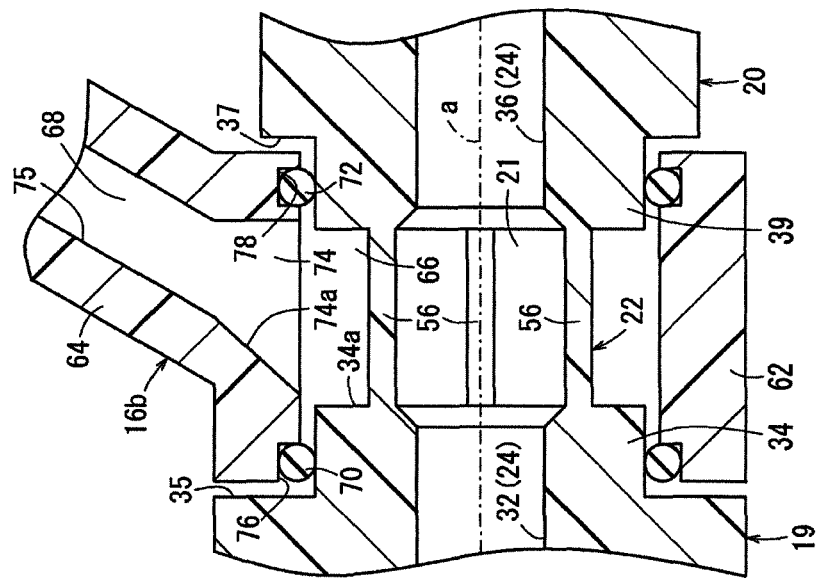
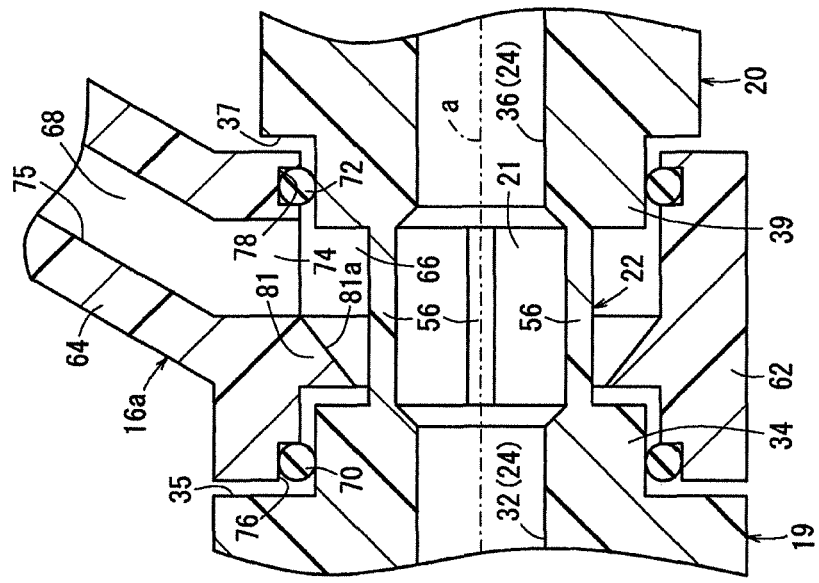

MEDICAL CONNECTOR

CROSS-REFERENCE TO RELATED APPLICATIONS

This application is a continuation of International Application Number PCT/JP2011/079651, filed on Dec. 21, 2011, which claims priority from JP 2011-039159, filed on Feb. 25, 2011, which are hereby incorporated herein by reference in their entirety.

FIELD OF THE INVENTION

The present invention relates to a medical connector connected to a proximal end portion of and used together with a tubular medical device.

BACKGROUND OF THE INVENTION

In order to treat a blood vessel (vasculature) abnormally narrowed by arteriosclerosis or the like, percutaneous transluminal coronary angioplasty (PTCA) is applied wherein a catheter having a dilation body at a distal end portion thereof is inserted into a stenosed site and the dilation body is inflated to expand the stenosed site thereby to improve the peripheral blood flow. This technique is carried out generally in the following manner. In particular, before a catheter with a dilation body (balloon catheter) is inserted into a blood vessel, a guiding catheter for introducing the catheter with the dilation body to the stenosed site is indwelled in the blood vessel. Then, the catheter with the dilation body is inserted through a Y connector which is a medical connector connected in advance to a proximal end portion of the guiding catheter.

A conventional Y connector includes a connector main body in which a lumen is provided into which the catheter with the dilation body can be inserted, and a branch which branches from a side face of the connector main body and has a side port provided at a distal end thereof. The branch is provided integrally with a body portion of the connector main body. At one end of the connector main body, a connection portion configured for connection to a proximal end portion of a guide catheter is provided for rotation around an axial line of the connector main body. At the other end of the connector main body, a cap portion rotatable around the axial line with respect to the connector main body is provided. Between the cap portion and the connector main body, a valve body is provided. The valve body is configured from an elastic member whose inner diameter varies in response to pressure applied thereto between the cap portion and the connector main body to open or close the lumen (refer to, for example, Japanese Patent No. 4472310).

SUMMARY OF THE INVENTION

When a Y-shaped connector configured in such a manner as described above is used, in order to supply liquid such as, for example, contrast agent to a guiding catheter connected to the Y connector, a liquid injection tool is connected to the side port. In this instance, if an adjustment to the direction of the side port is attempted in order to facilitate connection between the side port and the liquid injection tool, then a concern arises because the connector main body of the Y connector and the valve body (hemostasis valve) disposed in the interior of the Y connector for fixing a device such as a medical catheter are fixed against relative rotation. And since the connector main body and the branch are fixed against relative rotation, a device, such as a medical catheter, fixed to the valve body rotates together with rotation of the Y connector. If a device such as a medical catheter rotates, then the direction of the distal end portion thereof may change, so that there is a concern that the performance of a rapid procedure therewith will be negatively influenced.

The present invention has been made taking such a subject as described above into consideration, and it is an object of the present invention to provide a medical connector wherein the direction of a side port can be adjusted to an arbitrary direction as selected by the user without rotating a device such as a medical catheter inserted in a connector main body.

In order to achieve the object described above, according to one aspect of the present invention, there is provided a medical connector for being connected to a proximal end portion of a tubular medical device, the medical connector including a connector main body having a lumen formed therein so as to extend in a direction of an axial line and having, at one end thereof, a connection portion which is configured for connection to the proximal end portion of the medical device, and a branch provided so as to branch from the connector main body and having a side port connectable to a different device, a body portion of the connector main body having a communication path formed therein which provides communication between the interior and the exterior of the connector main body, the branch having a rotatable tubular portion having a liquid-tight, rotatable connection to the connector main body at a position at which the rotatable tubular portion covers the communication path and a branch lumen which forms a flow path from an inner circumferential face of the rotatable tubular portion to the side port and communicates with the lumen via the communication path.

According to the configuration of one aspect of the present invention, since the direction of the side port can be changed independently without rotating the main body, when a liquid injection tool is to be connected to the side port, it is possible to adjust the side port to be oriented to open in a selected direction. Consequently, connection of the liquid injection tool can be readily carried out. Further, even if the direction of the side port is changed, a device such as a medical catheter (for example, a balloon catheter) inserted in the main body will not rotate, and therefore, the procedure can be carried out smoothly.

Preferably, the medical connector described above is configured such that the communication path is provided at a plurality of locations in a circumferential direction of the connector main body.

According to the configuration described above, the cross-sectional area of the flow path, which provides communication between the lumen in the connector main body and the branch lumen, can be large, and movement of fluid from the branch to the connector main body can be carried out smoothly.

Preferably, the medical connector described above is configured such that a space extending annularly along the inner circumferential face of the rotatable tubular portion is formed between the rotatable tubular portion and the connector main body.

According to the configuration described above, the lumen and the branch lumen are always in reliable communication with each other through the space and the communication path irrespective of the positional relationship between the rotatable tubular portion and the connector main body in the circumferential direction. Therefore, the direction of the side port is not restricted, and connection of the liquid injection tool to the side port can be carried out more simply, easily, and thus rapidly.

Preferably, the medical connector described above is configured such that the connector main body includes a first element including the connection portion, a second element including the proximal end portion of the connector main body, and a connection portion which connects the first element and the second element so that they cannot rotate relative to each other and which has the communication path formed therein.

According to the configuration described above, different from the conventional medical connector, the connection portion does not have rotatable structure, and therefore, the total length of the connector main body can be reduced accordingly. Therefore, the effective length of a medical device (for example, a medical catheter) to be inserted into and used with the medical connector can be maximized.

More preferably, the medical connector described above is configured such that a first reduced diameter portion reduced in diameter and projecting in the direction of the axial line is provided at an end portion of the first element on the second element side; a second reduced diameter portion reduced in diameter and projecting in the direction of the axial line is provided at an end portion of the second element on the first element side; the inner circumferential face of the rotatable tubular portion and an outer circumferential face of the first reduced diameter portion have a liquid-tight seal therebetween provided by a first seal member; the inner circumferential face of the rotatable tubular portion and an outer circumferential face of the second reduced diameter portion have a liquid-tight seal therebetween provided by a second seal member; and the rotatable tubular portion is positioned in the direction of the axial line with respect to the connector main body between a side face of a step formed by the first reduced diameter portion and a side face of a step formed by the second reduced diameter portion.

According to the configuration described above, the rotatable tubular portion and the connector main body which can rotate relative to each other have a liquid-tight, rotatable connection therebetween, and the position of the rotatable tubular portion in the direction of the axial line with respect to the connector main body can be positioned suitably.

With the medical connector of one aspect of the present invention, the direction of the side port can be adjusted to a selected direction without rotating the medical device connected to the connector main body. Therefore, the medical procedure using the medical device can be carried out smoothly.

In another form, a medical connector is provided including an elongate main body having a longitudinal axis and a lumen extending axially therethrough, proximal and distal end portions of the elongate main body with the distal end portion being configured to be connected to a first tubular medical device, an auxiliary connection device having a port for being connected to a second tubular medical device, and an adjustable connection between the auxiliary connection device and the elongate main body that allows positioning of the port of the auxiliary connection device relative to the elongate main body to be adjustably selected by a user for ease in connecting the second tubular medical device to the auxiliary connection device.

In the above form, the elongate main body can have a generally tubular configuration, and the adjustable connection can be a rotatable connection to allow the auxiliary connection device to be circumferentially adjusted about the tubular, elongate main body.

In the above form, the tubular, elongate main body can have an annular recess extending thereabout, and the rotatable connection can be disposed in the annular recess.

In the above form, the auxiliary connection device can include a lumen extending therethrough and an opening thereof generally at or adjacent the rotatable connection, and the elongate main body can have a portion thereof configured to form a radial flow path between the main body lumen and the opening of the auxiliary connection device lumen irrespective of the circumferential position of the auxiliary connection device about the tubular, elongate main body.

In the above form, the auxiliary connection device can include an annular foot portion having the lumen opening formed therein, and the elongate main body can have an annular space extending about the main body portion with the annular foot portion extending about the annular space so that the radial flow path includes radial flow through the annular space to the auxiliary connection device lumen opening.

In the above form, the elongate main body portion can include circumferentially spaced, axially extending body members forming gaps therebetween for forming the radial flow path between the main body lumen and the auxiliary connection device lumen opening.

In the above form, the elongate main body portion can be axially intermediate the main body proximal and distal end portions and be configured so that the proximal and distal end portions are rotationally fixed relative to each other.

In the above form, the rotatable connection can include a sealing mechanism to form a liquid-tight, rotatable connection between the auxiliary connection device and the elongate main body.

In the above form, the auxiliary connection device can be a branch member configured to generally extend obliquely relative to the longitudinal axis of the elongate main body.

In the above form, the main body proximal end portion can have a port configured for receiving a third tubular medical device extending through the main body lumen and the first tubular medical device connected to the distal end portion.

In another form, a medical connector for being connected to a proximal end portion of a tubular medical device is provided. The medical connector includes an elongate main body having a longitudinal axis and a lumen extending axially therethrough, a distal connection portion of the elongate main body configured for connection to the proximal end portion of the medical device, a branch extending away from the connector main body transverse to the longitudinal axis and having a lumen extending therethrough including a side port configured for connection to a different medical device, a body portion of the elongate main body configured for forming a flow path between the respective lumens of the main body and the branch, and a liquid-tight, rotatable connection between the branch and the elongate main body disposed axially along the elongate main body for allowing fluid flow between the respective lumens of the main body and the branch via the flow path formed by the body portion.

In the above form, the body portion can be configured to have a plurality of distinct openings spaced thereabout, so that the flow path is provided at a plurality of corresponding locations in a circumferential direction about the elongate main body.

In the above form, the elongate main body can have an annular space extending annularly along the rotatable connection.

In the above form, the connector main body can include a first element including the distal connection portion, a second element including a proximal end portion of the elongate main body, and connection portions of the body portion which interconnect and fix the first element and the second element against rotation relative to each other and are configured for forming the flow path.

In the above form, the elongate main body can have an annular recess formed by a first reduced diameter end portion of the first element that projects axially in a proximal direction, and a second reduced diameter end portion of the second element that projects axially in a distal direction, and the branch can have an annular foot portion received in the annular recess and which includes an opening to the branch lumen with the liquid tight, rotatable connection including at least one seal member disposed between one of the first and second reduced diameter end portions and the branch foot portion.

In another form, a method of using a medical connector is provided, the method including connecting a distal end portion of elongate main body of the medical connector to a proximal end portion of a first tubular medical device, adjusting a circumferential position of a branch of the medical connector about the main body to a selected circumferential position, and connecting a second tubular medical device to the branch at the selected circumferential position.

In the above form, the circumferential position of the branch may be adjusted by rotating the branch in a circumferential direction about the elongate main body via a rotatable connection between the branch and the elongate main body.

In the above form, the branch may be rotated without rotating the elongate main body or changing the orientation of the first tubular medical device connected thereto.

In the above form, the circumferential position of the branch may be adjusted by rotating an annular foot portion of the branch in an annular recess in the elongate main body.

In the above form, the first tubular medical device may be a guide catheter, and the second tubular medical device may be a liquid injection tool, and the method may further include inserting the guide catheter into an artery to a target region therein, and operating the liquid injection tool to supply contrast agent to the branch with the contrast agent flowing through respective lumens in the branch and the elongate main body via a flow path formed therebetween with the contrast agent flowing through the guide catheter to the target region in the artery.

BRIEF DESCRIPTION OF THE DRAWINGS

FIG. 6A is a vertical sectional view showing a rotatable tubular portion of a branch and circumferential elements according to a first modification; and FIG. 6B is a vertical sectional view showing a rotatable tubular portion of a branch and circumferential elements according to a second modification.

DETAILED DESCRIPTION OF THE PREFERRED EMBODIMENTS

In the following a preferred embodiment of a medical connector according to the present invention is described with reference to the accompanying drawing.

Figure 1:
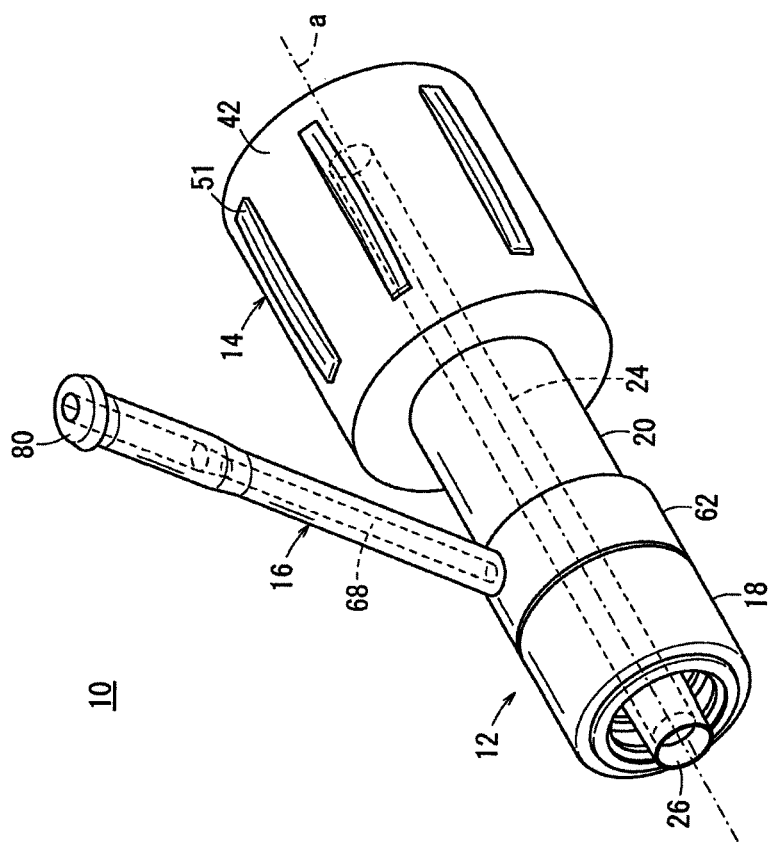
FIG. 1 is a perspective view of a medical connector according to an embodiment of the present invention.
Figure 2:
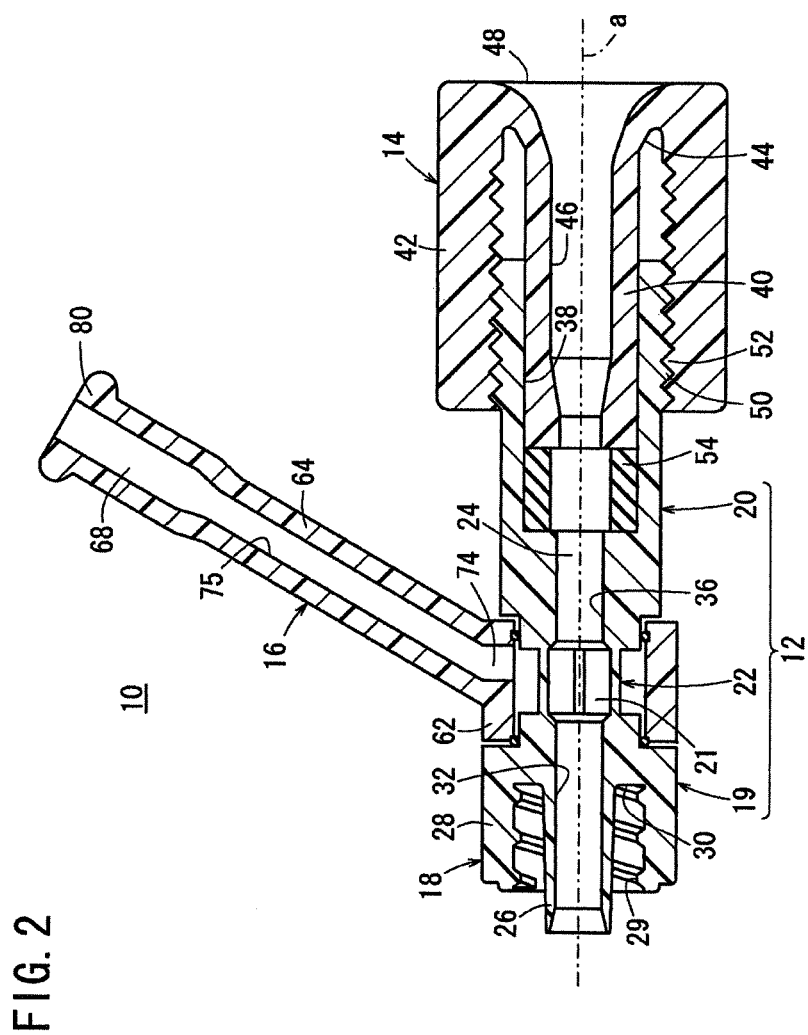
FIG. 2 is a vertical cross sectional view taken along a direction of an axial line of the medical connector shown in FIG. 1.
Figure 3:
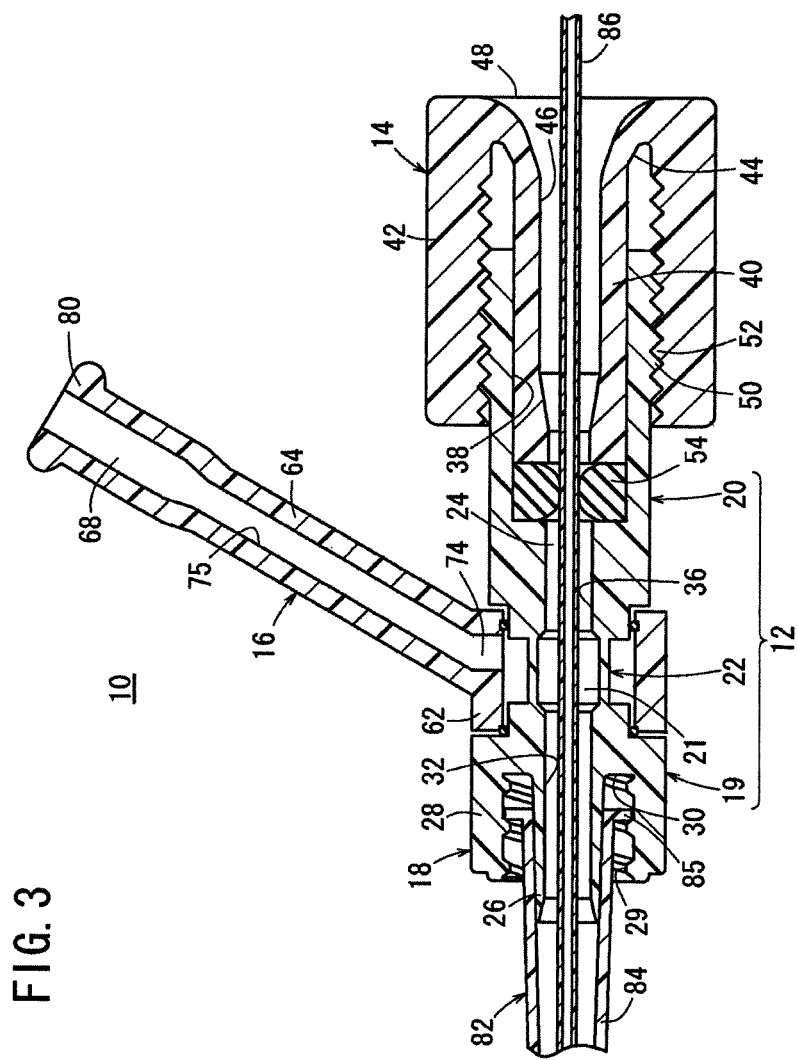
FIG. 3 is a vertical cross sectional view illustrating a use state of the medical connector shown in FIG. 1

FIG. 1 is a perspective view of a medical connector 10 according to an embodiment of the present invention; FIG. 2 is a vertical sectional view taken along a direction of an axial line a of the medical connector 10; and FIG. 3 is a vertical sectional view showing the medical connector 10 in a state in which it is connected to a hub 84 of a catheter 82.

The present medical connector 10 is connected to a proximal end portion (hub) of and used together with a tubular medical apparatus. The tubular medical apparatus to which the medical connector 10 is connected is a catheter 82 such as, for example, a guiding catheter or a medical catheter (for example, a balloon catheter or a thrombus aspiration catheter) (refer to FIG. 3).

Figure 4:
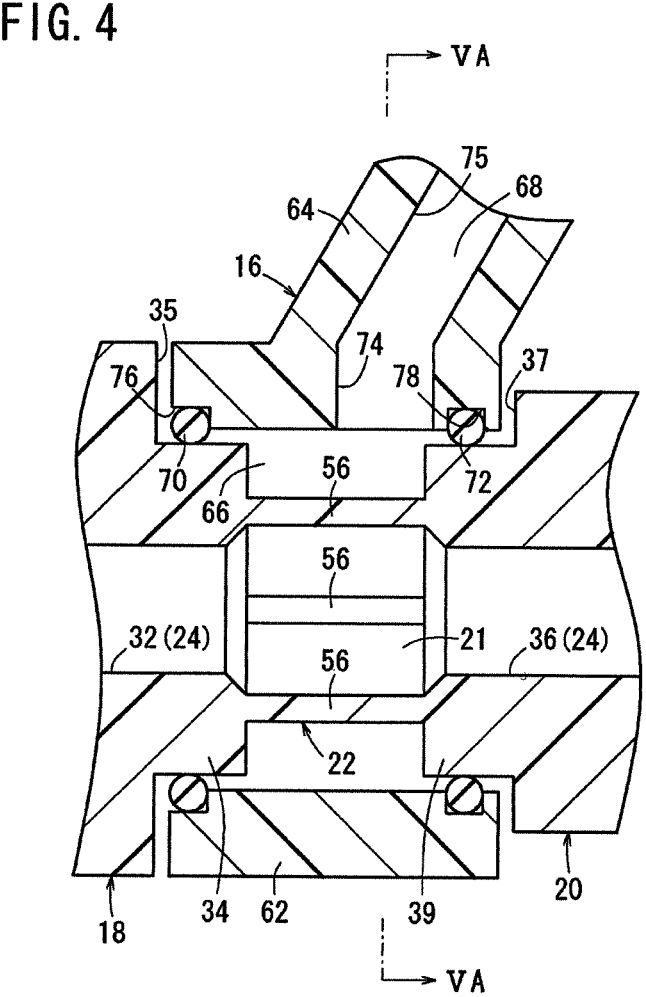
FIG. 4 is a partial enlarged sectional view of the medical connector shown in FIG. 1.

The medical connector 10 includes a connector main body 12, a cap member 14 provided at a proximal end portion of the connector main body 12, and a branch 16 which branches from the connector main body 12, and is configured as a Y connector of a generally Y shape. In the following, the configuration of the components of the medical connector 10 is described. It is to be noted that, for the convenience of description, the left side of the connector main body 12 in FIGS. 2, 3 and 4 is referred to as "distal end" and the right side is referred to as "proximal end (rear end)."

First, the configuration of the connector main body 12 is described. The connector main body 12 has a first element 19 including a connection portion 18 configured for connection to a hub 84 which is a proximal end portion of the catheter 82, and a second element 20 including a proximal end portion of the connector main body 12. The connector main body 12 further has a connection portion 22 which connects the first element 19 and the second element 20 against rotation relative to each other and having a communication path 21 formed therein, and a lumen 24 extending through the first element 19, the second element 20, and the connection portion 22 in the direction of an axial line or longitudinal axis a.

The first element 19 includes a distal end portion of the connector main body 12 and has a distal end tube portion 26, and a tubular portion 28 which concentrically surrounds the distal end tube portion 26 and has a female threaded portion 29 formed on an inner circumferential portion thereof. An annular recessed groove 30 which is open toward the distal end is formed radially between the distal end tube portion 26 and the tubular portion 28. A bore 32, which is configured as part of the lumen 24, is formed so as to extend through the first element 19 in the direction of the axial line a at the radial center of the first element 19. A first reduced diameter portion 34 (refer to FIG. 4) reduced in diameter and projecting in the direction of the axial line a is provided at a proximal end portion of the first element 19 (end portion on the second element 20 side).

The distal end tube portion 26 projects to the distal end side farther than the tubular portion 28 and has an outer diameter configured as a luer taper of a tapering shape whose diameter gradually decreases toward the distal end. Thus, when the distal end tube portion 26 is inserted into the hub 84 of the catheter 82 as shown in FIG. 3, the outer circumferential face of the distal end tube portion 26 and the inner circumferential face of the hub 84 have a liquid-tight fit with each other. The tubular portion 28 can be threadably fastened to a male threaded portion 85 provided at the proximal end of the hub 84 through the female threaded portion 29 provided on an inner circumferential portion thereof.

In the second element 20, a bore 36, which is configured as part of the lumen 24, is provided in the direction of the axial line a, and an expanded diameter portion 38 having an increased diameter with respect to that of the bore 36 is formed on the proximal end side with respect to the bore 36. At a distal end portion of the second element 20 (end portion on the first element 19 side), a second reduced diameter portion 39 (refer to FIG. 4) reduced in diameter and projecting in the direction of the axial line a is provided.

The cap member 14 is provided at a proximal end portion of the connector main body 12 (proximal end portion of the second element 20) for rotation around the axial line a with respect to the second element 20. The cap member 14 has an inner tube portion 40, and a rotationally operating portion 42 of a tubular shape which concentrically surrounds the inner tube portion 40. An annular recessed groove 44 which is open toward the distal end is formed radially between the inner tube portion 40 and the rotationally operating portion 42.

A bore 46 which is configured as part of the lumen 24 is formed in the inner tube portion 40 such that it extends through the inner tube portion 40 in the direction of the axial line a. The bore 46 is open, on the proximal end side of the cap member 14, as a port 48 which serves as an insertion opening for a catheter (for example, a medical catheter 86) different from the catheter 82 connected to the connector main body 12.

The rotationally operating portion 42 is configured for being gripped for rotation by a user (operator), and has non-slip ribs 51 raised outwardly in a radial direction and extending along the direction of the axial line a and which are formed in a spaced relationship from each other in a circumferential direction on an outer circumferential face of the rotationally operating portion 42.

As shown in FIG. 2, a female threaded portion 52 for being threaded to a male threaded portion 50 provided on the outer circumferential face of the proximal end of the second element 20 is formed on an inner circumferential portion of the rotationally operating portion 42. Therefore, if the rotationally operating portion 42 is rotated, then the rotationally operating portion 42 moves in the direction of the axial line a with respect to the connector main body 12 through the threaded engagement between the female threaded portion 52 and the male threaded portion 50.

A valve body 54 of a hollow tubular shape configured from an elastic member is disposed axially between the second element 20 and the inner tube portion 40. More particularly, the valve body 54 is disposed at the expanded diameter portion 38 of the second element 20 and is sandwiched between a step formed between the bore 36 and the expanded diameter portion 38 and a distal end face of the inner tube portion 40.

Although the material for the elastic member in the form of the valve body 54 is not limited, various rubbers such as, for example, silicone rubber, fluoro-rubber, isoprene and natural rubber, and various resins such as polyurethane, polyamide elastomer, polybutadiene and soft vinyl chloride or combinations of two or more of the materials may be used.

If the rotationally operating portion 42 is operated to rotate, then it advances toward the distal end while it rotates. Consequently, the valve body 54 is pressed to elastically deform in the direction of the axial line a by the inner tube portion 40 which moves in the direction toward the distal end, and as a result, the inner diameter of the valve body 54 decreases (refer to FIG. 3). If the rotationally operating portion 42 is rotated in the opposite direction, then the inner tube portion 40 is retracted and the pressure applied by the inner tube portion 40 against the valve body 54 is canceled, and consequently, the valve body 54 returns to its original shape by the elastic force thereof to thereby restore it to the state illustrated in FIG. 2.

Figure 5A:
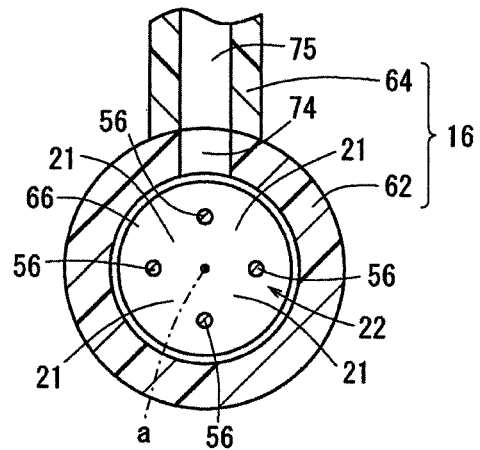
FIG. 5A is a transverse sectional view taken along line VA-VA of FIG. 4.

FIG. 4 is an enlarged vertical sectional view partly omitted of the connection portion 22 and peripheral elements of the connector main body 12, and FIG. 5A is a transverse sectional view taken along line VA-VA of FIG. 4. The connection portion 22 is an intermediate portion axially between the first element 19 and the second element 20, and includes the communication path 21 for providing communication between the interior and the exterior of the body portion of the connector main body 12.

As shown in FIGS. 4 and 5, in the medical connector 10 according to the present embodiment, the connection portion 22 has a plurality of rod-like connection bodies 56 extending along the direction of the axial line a and disposed in a spaced relationship from each other in a circumferential direction. The communication path 21 described above includes gaps formed between adjacent ones of the connection bodies 56. In the exemplary configuration shown, the connection bodies 56 are disposed at equal distances in the circumferential direction around the axial line a.

A boundary portion between the communication path 21 and the lumen 24 (portion at which the proximal end of an inner periphery of the connection portion 18 and the distal end of an inner periphery of the second element 20 face the communication path 21) is chamfered at an end portion thereof. By such a configuration as just described, catching of the distal end of the medical catheter at an angular end portion at the boundary portion between the communication path 21 and the lumen 24 can be avoided, and the medical catheter can be smoothly inserted into or removed from the lumen 24.

Figure 5B:
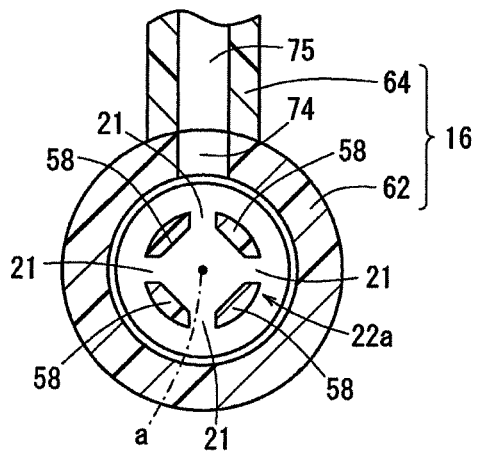
FIG. 5B is a transverse sectional view showing a connection portion and circumferential elements according to a first modification.
Figure 5C:
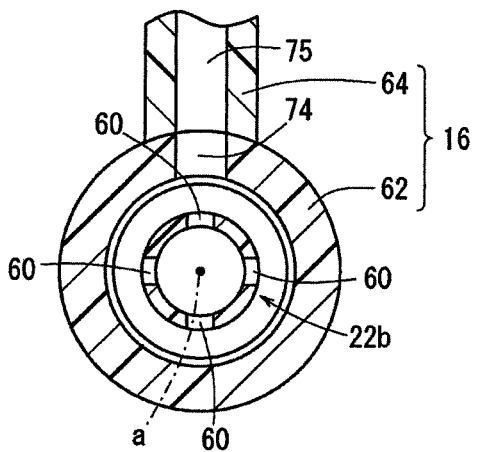
FIG. 5C is a transverse sectional view showing a connection portion and circumferential elements according to a second modification.

While the connection portion 22 shown in FIG. 5A has the rod-like connection bodies 56, it may otherwise have plate-like connection bodies 58 which extend along the direction of the axial line a and are spaced in a circumferential direction from each other like connection portions 22a according to a first modification shown in FIG. 5B. Or, it may otherwise be configured from a tubular member (in the example shown in FIG. 5C, a cylindrical member) having a plurality of hole portions 60 like connection portion 22b according to a second modification shown in FIG. 5C. In the case of the connection portion 22b, the hole portions 60 may be disposed in a zigzag pattern, a matrix pattern or the like spaced in both the circumferential direction and the axial direction of the axial line a.

Now, the configuration of the branch 16 is described. As shown in FIG. 2, the branch 16 has a rotatable tubular portion 62 having a rotatable, liquid-tight connection to the connector main body 12 for rotation with respect to the connector main body 12 at a position at which it covers the communication path 21, and a branch tubular portion 64 extending from the rotatable tubular portion 62. The branch 16 further has a side port 80 provided at a free end of the branch tubular portion 64 and connectable to a different device, and a branch lumen 68 which forms a flow path from the inner circumferential face of the rotatable tubular portion 62 to the side port 80 and communicates with the lumen 24 of the connector main body 12.

As shown in FIGS. 4 and 5A, the rotatable tubular portion 62 has a hollow cylindrical shape. The connection portion 22 described hereinabove is spaced from the inner circumferential face of the rotatable tubular portion 62 such that a space 66 which extends annularly along the inner circumferential face of the rotatable tubular portion 62, namely, in a range of 360 degrees around the axial line a, is formed between the rotatable tubular portion 62 and the connection portion 22. Therefore, the lumen 24 and the branch lumen 68 communicate with each other through the space 66 and the communication path 21.

A ring-shaped first seal member 70 configured, for example, as an O-ring is disposed between the inner circumferential face of the rotatable tubular portion 62 and the outer circumferential face of the first reduced diameter portion 34. A ring-shaped second seal member 72 configured, for example, as an O-ring is disposed between the inner circumferential face of the rotatable tubular portion 62 and the outer circumferential face of the second reduced diameter portion 39. The connector main body 12 and the rotatable tubular portion 62 are sealed liquid-tight therebetween by the first seal member 70 and the second seal member 72.

The first seal member 70 is disposed in a first annular groove portion 76 provided on an inner circumferential face of the rotatable tubular portion 62 on the distal end side with respect to a hole 74 which is part of the branch lumen 68. The second seal member 72 is disposed in a second annular groove portion 78 provided in the inner circumferential face of the rotatable tubular portion 62 on the proximal end side with respect to the hole 74.

In the exemplary configuration shown, the first annular groove portion 76 has a groove shape open to the distal end face and the inner circumferential face of the rotatable tubular portion 62. The second annular groove portion 78 has another groove shape open only to the inner circumferential face of the rotatable tubular portion 62. It is to be noted that the first annular groove portion 76 alternatively may have a groove shape open only to the inner circumferential face of the rotational tubular portion 62 similar to the second annular groove portion 78. The second annular groove portion 78 alternatively may have a groove shape open to the proximal end face and the circumferential face of the rotatable tubular portion 62.

The rotatable tubular portion 62 is positioned in the axial direction along the axial line a with respect to the connector main body 12 between a side face 35 of the step formed by the first reduced diameter portion 34 and the step formed by the second reduced diameter portion 39. In other words, on the connector main body 12, a recessed portion extending in a range of 360 degrees in the circumferential direction is formed from the first reduced diameter portion 34 and the second reduced diameter portion 39, and the rotatable tubular portion 62 is accommodated (mounted) in the recessed portion.

A bore 75 which is configured as part of the branch lumen 68 is formed in the branch tubular portion 64 to extend along the axial direction of the branch tubular portion 64. The bore 75 is open at the side port 80 provided at the free end (upper end in FIGS. 2, 3 and 5) of the branch tubular portion 64. The side port 80 functions as a connection port for connecting a liquid injection tool, not shown, for injecting contrast agent.

Although the material of the connector main body 12, branch 16 and cap member 14 described above is not limited, a thermoplastic resin such as polycarbonate, polyamide, polysulfone, polyallylate, methacrylate butylene styrene copolymer or the like can preferably be used.

The medical connector 10 according to the present embodiment is basically configured in such a manner as described above, and the following is a description of the operation and effects of the medical connector 10. In the following description, a method of use of the medical connector 10 is described in the case in which the medical connector 10 is connected to a hub of a guiding catheter which is used when percutaneous transluminal coronary angioplasty (PTCA) is carried out, for example.

When PTCA is carried out, the medical connector 10 is connected to the hub 84 of and used together with the catheter 82 as shown in FIG. 3. In this instance, the connector main body 12 and the hub 84 are threadably engaged to be integrally fixed to each other as described hereinabove. Here, the catheter 82 is configured as a guiding catheter to be used for PTCA.

First, a catheter introducer (hereinafter referred to as "introducer") not shown is operated to puncture an artery (blood vessel) by a Seldinger technique. Then, a guide wire, not shown, is inserted into the medical connector 10 and the catheter 82 through the port 48, and the catheter 82 in the state in which the guide wire is inserted is inserted into the introducer.

Then, in a state in which the guide wire precedes the distal end of the catheter 82, the distal end of the catheter 82 is inserted into the artery through the introducer until a distal end portion of the catheter 82 is engaged with a coronary artery ostium (right coronary artery ostium or left coronary artery ostium) through the aorta, and then the position of the distal end portion of the catheter 82 is fixed.

It is to be noted that, also in a Seldinger method in which a guiding sheath is used in place of an introducer, the medical connector of the present invention can be used in a similar manner.

After the distal end portion of the catheter 82 is engaged with the coronary artery ostium, the guide wire is removed from the catheter 82 and the medical connector 10, and a liquid injection tool for injecting contrast agent is connected to the side port 80 of the branch 16. In this instance, since the branch 16 is rotatable around the axial line or axis a of the connector main body 12, the operator can adjust the branch 16 to extend in a selected direction and then connect the liquid injection tool to the side port 80.

Then, the operator would operate the liquid injection tool to supply the contrast agent to the branch 16 of the medical connector 10. In this instance, since the branch lumen 68 and the lumen 24 communicate with each other through the communication path 21 formed in the connection portion 22, the contrast agent introduced from the liquid injection tool into the branch 16 is introduced into the catheter 82 through the communication path 21 of the medical connector 10 and the lumen 24, passes the lumen in the catheter 82 and is directed into the coronary artery of the target region. Consequently, confirmation of the insertion position of the distal end portion of the catheter 82 into the coronary artery ostium and imaging of the coronary artery become possible.

After the injection of the contrast agent, a medical catheter such as a PTCA balloon catheter is inserted into the coronary artery through the lumen 24 in the connector main body 12 and the lumen in the catheter 82. Then, a predetermined treatment (for example, expansion of the narrow part) is carried out using the medical catheter.

With the medical connector 10 according to the present embodiment, since the direction of the side port 80 can be changed independently without rotating the connector main body 12, when the liquid injection tool is connected to the side port 80, it is possible to adjust the side port 80 to a selected direction to readily carry out connection of the liquid injection tool.

Further, even if the direction of the side port 80 is changed, since the medical catheter inserted in the connector main body 12 does not rotate, the direction or the position of the distal end of the medical catheter can be prevented from changing. In other words, even if the direction of the side port 80 is changed, the direction of the distal end portion of the catheter 82 is maintained and the direction or the position of the distal end of the medical catheter inserted in the connector main body 12 in the blood vessel can be maintained. Therefore, the procedure can be carried out smoothly.

In the medical connector 10 according to the present embodiment, since the communication path 21 is provided at a plurality of locations in the circumferential direction of the connector main body 12, the cross-sectional area of the flow path providing communication between the lumen 24 in the connector main body 12 and the branch lumen 68 in the branch 16 can be maximized. Consequently, the movement of the fluid from the branch 16 to the connector main body 12 can be carried out smoothly.

In the medical connector 10 according to the present embodiment, since the space 66 which annularly extends along the inner circumferential face of the rotatable tubular portion 62 is formed between the rotatable tubular portion 62 and the communication path 21, the lumen 24 and the branch lumen 68 communicate with each other with certainty through the space 66 and the communication path 21 irrespective of the positional relationship between the rotatable tubular portion 62 and the communication path 21 in the circumferential direction. Therefore, the direction of the side port 80 is not restricted, and the connection of the liquid injection tool described above can be carried out simply, easily and rapidly.

In the medical connector 10 according to the present embodiment, the connector main body 12 is configured such that the first element 19 and the second element 20 are connected to each other to be fixed against relative rotation by the connection portion 22, which is different from the conventional medical connector 10, since the connection portion 18 does not have rotatable structure, the overall length of the connector main body 12 can be reduced accordingly. Therefore, the effective length of the medical device (for example, a medical catheter) to be inserted into and used together with the medical connector 10 can be maximized.

In the medical connector 10 according to the present embodiment, the rotatable tubular portion 62 is positioned in the direction of the axial line a with respect to the connector main body 12 between the side face 35 of the step formed by the first reduced diameter portion 34 and a side face 37 of the step by the second reduced diameter portion 39. Therefore, the rotatable tubular portion 62 and the connector main body 12 which can rotate relative to each other can be maintained with a secure, liquid-tight arrangement therebetween, and the axial position of the rotatable tubular portion 62 in the direction of the axial line a with respect to the connector main body 12 can be suitably identified.

A branch 16a according to a first modification shown in FIG. 6A may be adopted in place of the branch 16 described hereinabove. The branch 16a according to the first modification is different from the branch 16 described hereinabove in that a fluid guide portion 81 is provided on an inner circumferential portion of the rotatable tubular portion 62. The fluid guide portion 81 projects radially toward the connection portion 22 and is positioned on the first element 19 side with respect to the hole 74 which is open on the inner circumferential portion of the rotatable tubular portion 62 of the branch lumen 68. Further, an inner circumferential face 81a is formed such that it is displaced relative to the connection portion 22 from the second element 20 side toward the first element 19 side.

The fluid guide portion 81 shown in FIG. 6A particularly has a ring shape extending in a circumferential direction on the inner circumferential portion of the rotatable tubular portion 62, and the inner circumferential face 81a decreases in diameter from the second element 20 side toward the first element 19 side. With respect to the direction of the axial line a, preferably the position of the proximal end of the fluid guide portion 81 is positioned at the same position as or at a position proximate to the inner wall face of the hole 74 on the first element 19 side.

According to the configuration shown in FIG. 6A, when liquid (contrast agent or the like) is moved from the lumen of the branch 16 to the connector main body 12, the liquid can be moved smoothly along the fluid guide portion 81. In particular, by the provision of the fluid guide portion 81, retention of the flow is less likely to occur on the distal end side of the space 66 between the rotatable tubular portion 62 and the connection portion 22 in comparison with the alternative configuration which does not have the fluid guide portion 81 (refer to FIG. 4). Consequently, movement of the fluid from the branch lumen 68 to the connector main body 12 can be promoted.

A branch 16b according to a second modification shown in FIG. 6B may be adopted in place of the branch 16 described above. The branch 16 according to the second modification is different from the branch 16 described hereinabove in the shape of the hole 74 which is part of the branch lumen 68. In particular, an inner wall face 74a on the first element 19 side is formed so as to be displaced relative to the connection portion 22 side from the second element 20 side toward the first element 19. The inner wall face 74a is inclined in a tapering manner with respect to the axial line a, and the most distal end of the inner wall face 74a is positioned in the proximity of an end face 34a (face opposing to the second reduced diameter portion 39) of the first reduced diameter portion 34.

With the configuration shown in FIG. 6B, when liquid (contrast agent or the like) is moved from the branch lumen 68 to the connector main body 12, the liquid can be moved smoothly by the inner wall face 74a having the tapering form. In particular, since the inner wall face 74a having the tapering form is provided in the hole 74 which provides the opening of the branch lumen 68 on the connector main body 12 side, retention of the flow is less likely to occur on the distal end side of the space 66 between the rotatable tubular portion 62 and the connection portion 22 in comparison with the alternative configuration which does not have the inner wall face 74a (refer to FIG. 4). Consequently, movement of the liquid from the branch lumen 68 to the connector main body 12 can be promoted.

Figure 7A:
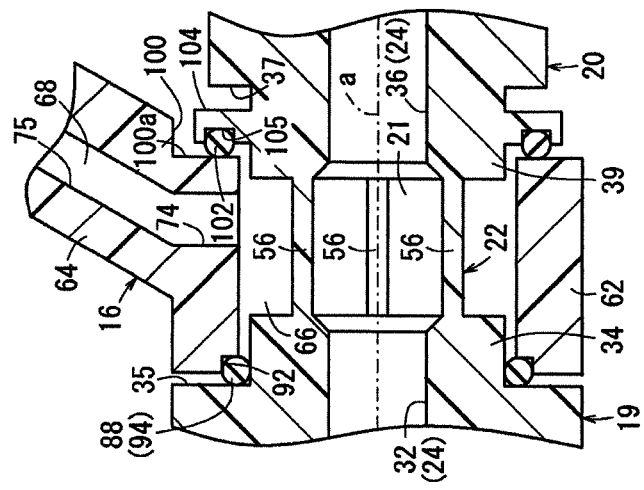
FIG. 7A is a vertical sectional view showing a seal structure and circumferential elements according to a first modification.
Figure 7B:
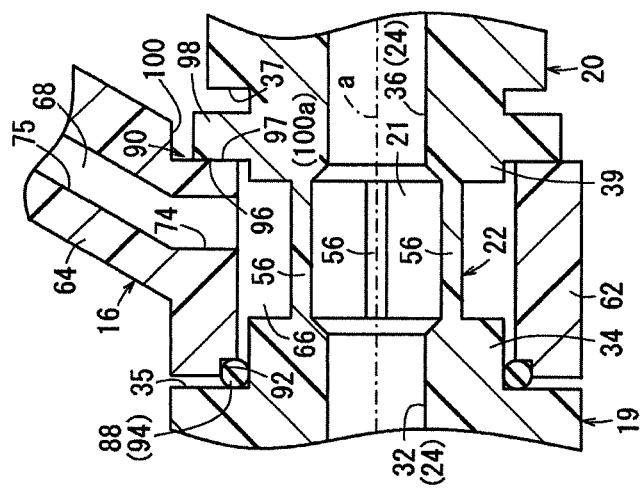
FIG. 7B is a vertical sectional view showing a seal structure and circumferential elements according to a second modification.
Figure 7C:
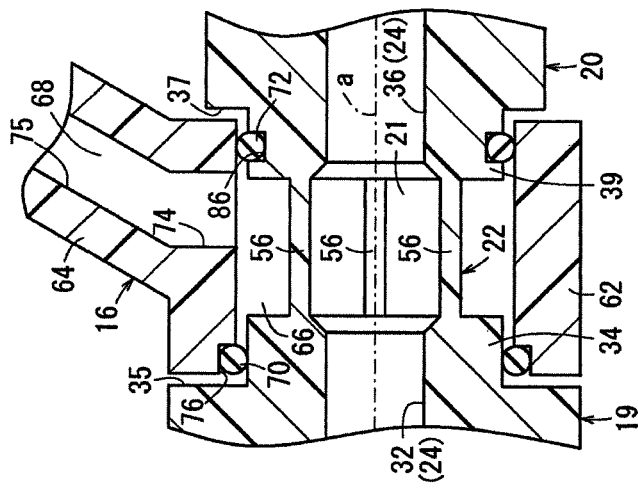
FIG. 7C is a vertical sectional view showing a seal structure and circumferential elements according to a third modification.

Seal structures shown in FIGS. 7A to 7C may be adopted in place of the seal structure between the connector main body 12 and the rotatable tubular portion 62 shown in FIG. 4. The seal structure shown in FIG. 7A includes a first seal member 70 and a second seal member 72 similar to that shown in FIG. 4. However, different from the seal structure of FIG. 4, in the seal structure shown in FIG. 7A, a second annular groove portion 86 is provided on an outer circumferential portion of the second reduced diameter portion 39 of the second element 20. The function and the operation of the first seal member 70 and the second seal member 72 in the seal structure shown in FIG. 7A are similar to the function and the operation of the first seal member 70 and the second seal member 72 in the seal structure shown in FIG. 4, respectively.

The seal structure shown in FIG. 7B has a first seal portion 88 and a second seal portion 90 provided between the connector main body 12 and the rotatable tubular portion 62. The first seal portion 88 is provided at a position of the branch lumen 68 on the distal end side with respect to the hole 74 which is open to the inner circumferential portion of the rotatable tubular portion 62. In particular, the first seal portion 88 is a ring-shaped seal member 94 made of elastic material and mounted in an annular groove portion 92 provided at an angular portion between the inner circumferential face and a distal end face of the rotatable tubular portion 62. The seal member 94 is configured similarly to the first seal member 70 shown in FIG. 4. The seal member 94 is sandwiched from the opposite sides in the direction of the axial line a by and between the outer circumferential face of the first reduced diameter portion 34 and the annular groove portion 92 and is sandwiched in a radial direction by and between the side face 35 of the step formed by the first reduced diameter portion 34 and the annular groove portion 92 and is held in an elastically compressed state.

Then second seal portion 90 is provided at a position on the proximal end side with respect to the hole 74 and is configured by close contact between a first sliding face 96 extending in a circumferential direction and a radial direction on the connector main body 12 and a second sliding face 97 extending in a circumferential direction and a radial direction on the rotatable tubular portion 62. The second sliding face 97 is pressed against the first sliding face 96 by the elastic force (resilient force) of the seal member 94. Consequently, the first sliding face 96 and the second sliding face 97 contact each other in a liquid-tight manner. In the configuration example of FIG. 7B, the first sliding face 96 is formed from a distal end face of an annular projection 98 which projects outwardly in a radial direction from an outer circumferential portion of the second reduced diameter portion 39 and extends in a circumferential direction. The second sliding face 97 is formed from a side face 100a of an annular step 100 provided on the proximal end of the rotatable tubular portion 62.

According to the seal structure of FIG. 7B, since only one seal member 94 is disposed between the rotational tubular portion 62 and the connector main body 12, the number of parts can be reduced and the configuration can be simplified in comparison with the configuration of FIG. 4. Further, since the first sliding face 96 and the second sliding face 97 closely contact with each other favorably by the elastic force of the seal member 94, a good sealing effect is exhibited also by the second seal portion 90 where the seal member 94 is not disposed.

It is to be noted that a configuration wherein the disposition of the first seal portion 88 and the second seal portion 90 is changed may be adopted. In particular, a configuration is contemplated wherein the second seal portion 90 is reversed forwardly and rearwardly and may be provided on the distal end side of the rotatable tubular portion 62, and wherein the first seal portion 88 is reversed forwardly and rearwardly and may be provided on the proximal end side of the rotatable tubular portion 62.

The seal structure shown in FIG. 7C has a seal member 94 and a second seal member 102 provided between the connector main body 12 and the rotatable tubular portion 62. The first seal member 94 and the mounting structure for the first seal member 94 are same as the seal member 94 and the mounting structure of the seal member 94 shown in FIG. 7B. The second seal member 102 is sandwiched by and between the connector main body 12 and the rotatable tubular portion 62 from the opposite sides in the direction of the axial line a at a position on the proximal end side in the direction of the axial line a with respect to the hole 74 and is held in an elastically compressed state. In particular, an annular seal mounting groove 105 extending in a circumferential direction is formed on a distal end face of an annular projection 104 which projects outwardly in a radial direction from an outer circumferential portion of the second reduced diameter portion 39 and extends in a circumferential direction. The second seal member 102 is mounted in the seal mounting groove 105. The second seal member 102 is sandwiched by and between a side face 100a of an annular step 100 provided on the proximal end of the rotatable tubular portion 62 and the seal mounting groove 105. By the elastic force of the first seal member 94, the side face 100a and the second seal member 102 have a closely contacting, liquid-tight engagement with each other, and the second seal member 102 and the seal mounting groove 105 have a closely contacting liquid-tight engagement with each other. Further, by the elastic force of the second seal member 102, the side face 35 of the step formed by the first reduced diameter portion 34 and the first seal member 94 have a closely contacting liquid-tight engagement with each other and the first seal member 94 and the annular groove portion 92 have a closely contacting liquid-tight engagement with each other.

According to the seal structure of FIG. 7C, the close contacting engagement of the second seal member 102 can be enhanced by the elastic force of the first seal member 94, and the close contacting engagement of the first seal member 94 can be enhanced by the elastic force of the second seal member 102. Consequently, a better sealing effect is exhibited by a synergetic effect of the seal members, and a superior liquid leak prevention effect can be achieved.

It is to be noted that a configuration wherein the mounting structure of the first seal member 94 and the mounting structure of the second seal member 102 are exchanged may be adopted. In particular, a configuration may be adapted wherein the mounting structure of the second seal member 102 is reversed forwardly and rearwardly and may be provided on the distal end of the rotatable tubular portion 62, and wherein the mounting structure of the first seal member 94 is reversed forwardly and reversely and may be provided on the proximal end of the rotational tubular portion 62.

While the preferred embodiment of the present invention has been described above, the present invention is not limited to the embodiment described above and it is manifest that various modifications are possible without departing from the subject matter of the present invention.

The invention claimed is:

1. A medical connector for being connected to a proximal end portion of a tubular medical device, the medical connector comprising:
   an elongate main body having a longitudinal axis and a lumen extending axially therethrough;
   a distal connection portion of the elongate main body configured for connection to the proximal end portion of the medical device;
   a branch configured to be freely rotatable with respect to the connector main body and extending away from the connector main body transverse to the longitudinal axis and having a lumen extending therethrough including a proximal side port configured for connection to a different medical device and a distal opening for establishing a flow path with the elongate main body lumen;
   a body portion of the elongate main body configured for forming the flow path between the respective lumens of the main body and the branch;
   a liquid-tight, rotatable connection between the branch and the elongate main body disposed axially along the elongate main body for allowing fluid flow between the respective lumens of the main body and the branch via the flow path formed by the body portion;
   wherein the body portion has a plurality of distinct openings spaced thereabout so that the flow path is provided at a plurality of corresponding locations in a circumferential direction about the elongate main body;

wherein the branch has a rotatable tubular portion having the liquid-tight, rotatable connection to the connector main body;

wherein the rotatable tubular portion includes the branch distal opening and extends about the body portion and the distinct openings thereof to cover the flow path on an outer circumferential surface of the body portion; and wherein a branch tubular portion of the branch extends from the rotatable tubular portion.

2. The medical connector according to claim 1, wherein the elongate main body has an annular space extending annularly about the outer circumferential surface of the body portion in a rotary direction of the rotatable tubular portion along the rotatable connection.

3. The medical connector according to claim 1, wherein the elongate main body includes a first element including the distal connection portion, a second element including a proximal end portion of the elongate main body, and connection portions of the body portion which interconnect and fix the first element and the second element against rotation relative to each other and are configured for forming the flow path with the connector portions having the distinct openings formed therebetween.

4. The medical connection according to claim 3, wherein the elongate main body has an annular recess formed by a first reduced diameter end portion of the first element that projects axially in a proximal direction, and a second reduced diameter end portion of the second element that projects axially in a distal direction, and wherein the branch rotatable tubular portion comprises an annular foot portion received in the annular recess and which includes the distal opening of the branch lumen with the liquid tight, rotatable connection including at least one seal member disposed between one of the first and second reduced diameter end portions and the branch foot portion.

5. The medical connector according to claim 1 wherein the rotatable connection is at a predetermined axial location along the elongate main body so that rotation of the branch including the rotatable tubular portion thereof occurs at the predetermined axial location without causing the branch to shift axially away therefrom along the elongate main body.

6. The medical connector according to claim 1 wherein the rotatable connection comprises a non-threaded rotatable connection.

7. The medical connector according to claim 1 wherein the outer circumferential surface of the body portion includes a plurality of outer surface portions circumferentially spaced by the plurality of distinct openings therebetween.

8. A method of using a medical connector, the method comprising:

connecting a distal end portion of elongate main body of the medical connector to a proximal end portion of a first tubular medical device;

adjusting a circumferential position of a branch of the medical connector about the main body to a selected circumferential position;

connecting a second tubular medical device to the branch at the selected circumferential position;

wherein the circumferential position of the branch is adjusted by rotating the branch in a circumferential direction about the elongate main body via a rotatable connection between the branch and the elongate main body;

wherein the branch has a rotatable tubular portion having the rotatable connection to the main body; and wherein the rotatable tubular portion is positioned to extend about an outer circumferential surface of the main body to be freely rotatable thereabout.

9. The method of claim 8 wherein the branch is rotated without rotating the elongate main body or changing the orientation of the first tubular medical device connected thereto.

10. The method of claim 8 wherein the rotatable tubular portion comprises an annular foot portion of the branch, and the circumferential position of the branch is adjusted by rotating the annular foot portion of the branch in an annular recess in the elongate main body.

11. The method of claim 8 wherein the first tubular medical device is a guide catheter, and the second tubular medical device is a liquid injection tool, and further comprising:

inserting the guide catheter into an artery to a target region therein, and operating the liquid injection tool to supply contrast agent to the branch with the contrast agent flowing through respective lumens in the branch and the elongate main body via a flow path formed therebetween with the contrast agent flowing through the guide catheter to the target region in the artery.

12. The method of claim 8 wherein the main body outer circumferential surface includes a plurality of outer surface portions circumferentially spaced by a plurality of distinct openings of the main body circumferentially spaced thereabout.

* * * * *